United States Patent [19]

Kirby et al.

[11] Patent Number: 5,259,367
[45] Date of Patent: Nov. 9, 1993

[54] DEVICES AND METHODS FOR PLACEMENT OF FEEDING TUBES

[75] Inventors: Donald F. Kirby, Richmond, Va.; Lester D. Michels, Eden Prairie; Frederick K. Reuning, Minnetonka, both of Minn.

[73] Assignee: Sandoz Ltd., Basel, Switzerland

[21] Appl. No.: 783,051

[22] Filed: Oct. 25, 1991

[51] Int. Cl.$^5$ .............................. A61B 1/26
[52] U.S. Cl. .............................. 128/8; 604/175; 215/307
[58] Field of Search ............ 128/8; 604/174, 178, 604/175, 283, 54, 167; 215/307, 358, 364, 308

[56] References Cited

U.S. PATENT DOCUMENTS

| | | | |
|---|---|---|---|
| 1,760,841 | 5/1930 | Garhart | 215/307 X |
| 2,884,151 | 4/1959 | Biederman | 215/307 X |
| 3,317,274 | 5/1967 | McCormick | 215/307 X |
| 3,339,772 | 9/1967 | Miller | 215/307 X |
| 3,656,485 | 4/1972 | Robertson | 128/8 X |
| 3,915,171 | 10/1975 | Shermeta | 128/368 X |
| 4,668,225 | 5/1987 | Russo et al. | 604/104 X |
| 4,726,374 | 2/1988 | Bales et al. | |
| 4,798,592 | 1/1989 | Parks | 128/DIG. 26 X |
| 4,826,481 | 5/1989 | Sacks et al. | 604/164 X |
| 4,863,438 | 9/1989 | Gauderer et al. | 604/175 X |
| 4,874,365 | 10/1989 | Frederick et al. | 604/54 |
| 4,944,732 | 7/1990 | Russo | 604/175 X |
| 5,007,900 | 4/1991 | Richa et al. | 604/175 X |
| 5,073,166 | 12/1991 | Parks et al. | 604/174 X |
| 5,074,846 | 12/1991 | Clegg et al. | 604/283 X |
| 5,084,014 | 1/1992 | Picha et al. | 604/175 X |
| 5,092,850 | 3/1992 | Buma | 604/175 |

FOREIGN PATENT DOCUMENTS

| | | |
|---|---|---|
| 0256546 | 2/1988 | European Pat. Off. |
| 0370720 | 5/1990 | European Pat. Off. |
| 9112338 | 11/1991 | Fed. Rep. of Germany |

OTHER PUBLICATIONS

T. Russell, et al., The American Journal of Surgery, vol. 148, pp. 132-137 (Jul. 1984).

*Primary Examiner*—Robert Bahr
*Assistant Examiner*—Karen A. Jalbert
*Attorney, Agent, or Firm*—Robert S. Honor; Melvyn M. Kassenoff; Carl W. Battle

[57] ABSTRACT

Method for placing a guide wire through a gastrostomy tube which has a plug through which only the guide wire can pass in slidable communication. The plug prevents air from escaping from the stomach, thus, preventing the collapse of the stomach during the guide wire placement. The plug may comprise a substantially cylindrical member having a longitudinal bore for receiving the guide wire in slidable communication.

6 Claims, 1 Drawing Sheet

DEVICES AND METHODS FOR PLACEMENT OF FEEDING TUBES

FIELD OF THE INVENTION

This invention relates to devices and methods for the placement of gastrostomy-jejunal feeding tubes which are receivable through the wall of the stomach for the enteral feeding of patients.

BACKGROUND AND SUMMARY OF THE INVENTION

The use of feeding tubes which extend directly into the stomachs of patients is often required when patients cannot swallow or when they have strictures in their esophagi which prevent food from entering into their stomachs. In situations of this type, it is common to perform surgical procedures such as a percutaneous endoscopic gastrostomy (PEG) on the patient. In this procedure (PEG) an opening is formed in the skin, fascia and stomach wall and a gastrostomy tube is installed in the opening to allow food and/or medication to be passed directly into the stomach, and also to allow fluids to be drained therefrom.

When there is a need for direct intestinal feeding, one surgical procedure is to first install the gastrostomy tube and inflate the stomach with air. Then a guide wire is passed through the gastrostomy tube into the stomach where it is grasped with grasping forceps and dragged into the small intestine. The jejunal tube is then passed over the guide wire into the small intestine. When the feeding tube is in place, the wire can be removed and the patient can be fed.

However, the placement of the guide wire is difficult because the stomach collapses due to the escape of air through the gastrostomy tube. The deflation of the stomach makes it difficult for the Endoscopist to find the pylorus and the opening to the small intestine.

Thus, there is a need for a method of placing the guide wire in the small intestine without the deflation of the stomach.

The present inventive procedure is to place the guide wire through the gastrostomy tube which has a plug through which only the guide wire can pass. The stomach is inflated with air which is substantially prevented from escaping through gastrostomy tube by the plug, and the guide wire is pulled through the plug for placement. When the wire is in place in the small intestine, the plug is removed from the gastrostomy tube and a feeding tube is then passed over the guide wire into the small intestine. When the tube is in place, the wire is removed and feeding can take place.

The plug may comprise a substantially cylindrical member having a longitudinal bore for receiving the guide wire in slidable communication with the bore.

DESCRIPTION OF THE DRAWINGS

In the drawings which illustrate the best mode presently contemplated for carrying out the invention.

DESCRIPTION OF THE INVENTION

Figure 1:
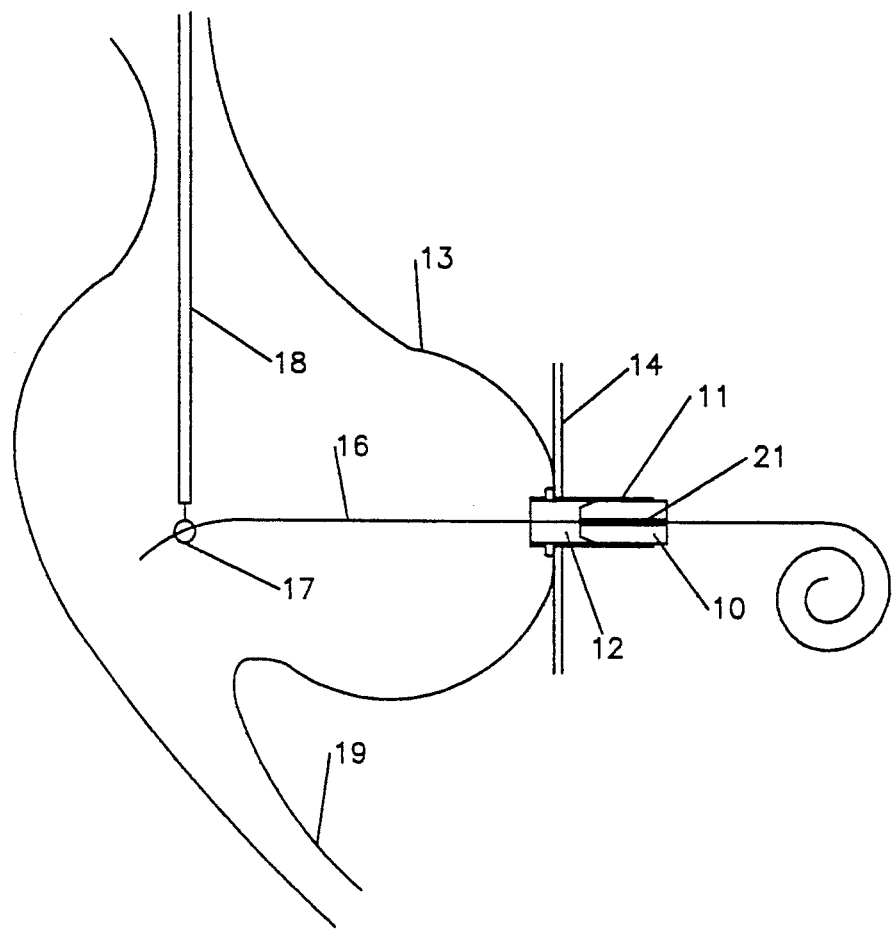
FIG. 1 is a fragmentary sectional view of a feeding tube guide wire installation in the stomach of a patient showing a gastrostomy tube plug of this invention.

Referring now to the drawings, a gastrostomy tube plug of this invention is illustrated in FIG. 1, showing the installation of a feeding tube guide wire. The plug 10 is shown installed in the external end 11 of a gastrostomy tube 12. The gastrostomy tube 12 is in place creating an opening between the stomach 13 and the patient's skin 14. A guide wire 16 is passed through the plug 10 and the gastrostomy tube 12 and into the air inflated stomach 13 where it is grasped by the grasping forceps 17 of an endoscope 18, to be placed in the small intestine 19.

The plug 10 may be a substantially cylindrical member and have a longitudinal bore 21 through which the guide wire 16 passes in slidable communication. The diameter of the bore 21 is such that it is larger than the diameter of the guide wire 16, to allow the movement of the guide wire 16 through it, but in slidable contact with the guide wire 16 to prevent any substantial amount of air from escaping from the stomach 13. As shown in FIG. 1, the plug 10 may have a solid core 22 with the longitudinal bore 21 through it.

Figure 2:
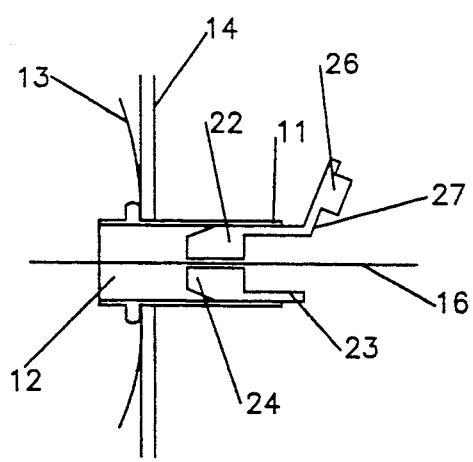
FIG. 2 is a sectional view of a preferred gastrostomy tube plug of this invention.

Preferably, as shown in FIG. 2, the solid core 22 does not traverse the length of the plug 10, allowing for a tube-like portion 23 of the plug. The opening of the tube 23 of the plug 10 may have a stopper 26 appendaged to it, by a flexible connector 27. The stopper 26, when inserted into the opening of the tube portion 23 prevents air leakage through the bore 21 from the stomach, before the guide wire 16 is inserted in the bore. The stopper 26 is preferably tapered to provide a friction fit within the tube portion 23. In a similar manner, the portion of the plug 10 engaging the gastrostomy tube 12 is preferably tapered to provide a friction fit with the gastrostomy tube 12 and thus, prevent an unwanted disconnection.

In operation, after the gastrostomy tube 12 is installed and the endoscope 18 is in place in the stomach 13, the stopped plug 10 is inserted in the gastrostomy tube 12 and the stomach is inflated with air. The stopper 26 is removed from the plug 10 and the guide wire 16 is inserted in the bore 21 of the plug and moved into the stomach where it is grasped by the grasping forceps 17 for insertion in the small intestine 19. When the guide wire 16 is in the desired place in the small intestine, the plug 10 is disengaged from the gastrostomy tube 12 and removed from the guide wire. A jejunal feeding tube (not shown) may then be placed over the guide wire 16 and positioned in the small intestine 19. The guide wire 16 is then removed and a conventional enteral feeding set (not shown) is connected to the jejunal feeding tube for feeding of the patient.

Figure 3:
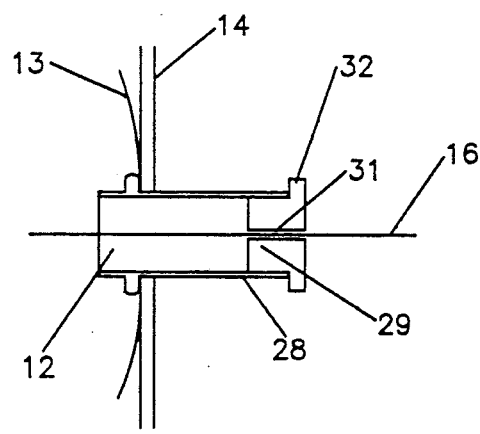
FIG. 3 is a sectional view of a variation of the gastrostomy tube plug of this invention.

The plug device of this invention may also be constructed as a semi-permanent part of the gastrostomy tube 12. As shown in FIG. 3, the external end 28 of the gastrostomy tube 12 may have a removable restricted opening 29 with a bore 31 therethrough. The bore 31 receives a guide wire in slidable engagement, and prevents substantial air escape from the stomach while the guide wire is placed in the small intestine. After placement of the guide wire, the restricted opening 29 may be removed by grasping the flange 32 and sliding it along the guide wire.

The devices of this invention may be prepared from conventional non-toxic elastomeric and plastic materials, e.g., silicon rubber.

What is claimed is:

1. A method for the prevention of air escaping from a stomach during the placement of a guide wire through a percutaneous gastrostomy tube which comprises providing a substantially cylindrical plug on an external end of said gastrostomy tube, wherein said plug has a longitudinal bore through which the guide wire passes in slidable communication while substantially preventing stomach air flow out of the gastrostomy tube, and placing said guide wire through said bore and said gastrostomy tube into said stomach.

2. The method according to claim 1 wherein said cylindrical plug member has a tube-like portion adapted to receive a stopper.

3. The method according to claim 2 wherein said stopper is appendaged to said tube-like portion of the cylindrical member by a flexible connector.

4. The method of claim 1 wherein said gastrostomy tube is first installed in the stomach and said stomach is inflated with air.

5. The method of claim 4 wherein said guide wire is subsequently inserted into the small intestine and said plug is removed from said gastrostomy tube.

6. A gastrostomy feeding device comprising a percutaneous gastrostomy tube, a feeding tube guide wire, and a device for preventing air leakage from the percutaneous gastrostomy tube during placement of the feeding tube guide wire through said gastrostomy including tube a substantially cylindrical plug member having a longitudinal bore for receiving the guide wire in slidable communication with the bore and a stopper appendaged to said plug member by a flexible connector, said plug being adaptable for removeable installation in the external end of said gastrostomy tube and having a tube-like portion adapted to receive said stopper.

* * * * *

UNITED STATES PATENT AND TRADEMARK OFFICE
CERTIFICATE OF CORRECTION

PATENT NO. : 5,259,367

DATED : November 9, 1993

INVENTOR(S) : Donald F. Kirby, Lester D. Michels and Frederick K. Reuning

It is certified that error appears in the above-identified patent and that said Letters Patent is hereby corrected as shown below:

Column 4, lines 7-18,

A gastrostomy feeding device comprising a percutaneous gastrostomy tube, a feeding tube guide wire, and a device for preventing air leakage from the percutaneous gastrostomy tube during placement of the feeding tube guide wire through said gastrostomy tube including a substantially cylindrical plug member having a longitudinal bore for receiving the guide wire in slidable communication with the bore and a stopper appendaged to said plug member by a flexible connector, said plug being adaptable for removeable installation in the external end of said gastrostomy tube and having a tube-like portion adapted to receive said stopper.

Signed and Sealed this

Second Day of August, 1994

Attest:

BRUCE LEHMAN

*Attesting Officer*    Commissioner of Patents and Trademarks